(12) United States Patent
Stahl et al.

(10) Patent No.: US 11,213,604 B2
(45) Date of Patent: Jan. 4, 2022

(54) COMPOSITION FOR DRESSING CUTANEOUS LESIONS AND MANUFACTURING METHOD THEREOF (71) Applicants: Kurt-Wilhelm Stahl, Freiburg (DE); Kurt Bauer, Freiburg (DE)

(72) Inventors: Kurt-Wilhelm Stahl, Freiburg (DE); Kurt Bauer, Freiburg (DE)

( * ) Notice: Subject to any disclaimer, the term of this patent is extended or adjusted under 35 U.S.C. 154(b) by 0 days.

(21) Appl. No.: 16/469,418

(22) PCT Filed: Dec. 13, 2017

(86) PCT No.: PCT/EP2017/082724
§ 371 (c)(1),
(2) Date: Jun. 13, 2019

(87) PCT Pub. No.: WO2018/109051
PCT Pub. Date: Jun. 21, 2018

(65) Prior Publication Data
US 2019/0381209 A1 Dec. 19, 2019

(30) Foreign Application Priority Data
Dec. 13, 2016 (WO) ............... PCT/EP2016/080861

(51) Int. Cl.
*A61L 26/00* (2006.01)
*A61K 9/00* (2006.01)
*A61K 9/70* (2006.01)

(52) U.S. Cl.
CPC ........ *A61L 26/0023* (2013.01); *A61K 9/0014* (2013.01); *A61K 9/7015* (2013.01); *A61L 26/0004* (2013.01)

(58) Field of Classification Search
None
See application file for complete search history.

(56) References Cited

U.S. PATENT DOCUMENTS

| 4,956,350 A | 9/1990 | Mosbey |
| 5,503,847 A | 4/1996 | Queen et al. |

(Continued)

FOREIGN PATENT DOCUMENTS

| EP | 0666081 A1 | 8/1995 |
| WO | WO-95/00184 A1 | 1/1995 |

(Continued)

OTHER PUBLICATIONS

International Search Report and written opinion report for patent application No. PCT/EP2017/082724, dated Apr. 24, 2018.

(Continued)

*Primary Examiner* — Kyung S Chang
(74) *Attorney, Agent, or Firm* — Moser Taboada (57) ABSTRACT The invention relates to a composition for dressing cutaneous lesions, in particular cutaneous leishmanial lesions or cutaneous lesions due to actinic keratosis, comprising, based on the total weight of the composition:—10.0 weight percent to 35 weight percent of a one or more diols, selected from the group comprising 1,2-propylene glycol, 1,2-pentanediol, 1,3-butanediol and 2,2'-[Ethane-1,2-diylbis(oxy)]di(ethan-1-ol),—2.0 weight percent to 20 weight percent of at least one first film-forming agent, selected from one or more of a cellulose derivative, hemicellulose, a hemicellulose derivative, chitosan, a chitosan derivative, or oligoglucosamines,—0.2 to 25.0 weight percent of at least one elastic second film-forming agent, selected from one or more thickening agents,—0.2 to 25.0 weight percent of one or more polymeric surfactants,—0.005 to 0.5 weight percent chlorate-free chlorite,—water adding up to 100.0 weight percent.

19 Claims, 1 Drawing Sheet (56) References Cited

U.S. PATENT DOCUMENTS 5,718,916 A 2/1998 Scherr
2009/0214628 A1* 8/2009 de Rijk .................. A61P 17/02
424/450

FOREIGN PATENT DOCUMENTS

| WO | WO-0019981 A1 | 4/2000 |
| WO | WO-01/64174 A1 | 9/2001 |

OTHER PUBLICATIONS

Written Opinion of PCT Application No. PCT/EP2017/082724, dated Nov. 29, 2018.

* cited by examiner

COMPOSITION FOR DRESSING CUTANEOUS LESIONS AND MANUFACTURING METHOD THEREOF

The invention relates to a composition for dressing cutaneous lesions, methods for preparing such a composition, methods for applying such a composition to the lesions, as well as containers and kits comprising such compositions.

BACKGROUND OF THE INVENTION

Cutaneous lesions can occur due to a variety of reasons, for example injuries, autoimmune reactions, metabolic disorders, such as diabetes, a generally decreased physical status in particular in elderly patients, which therefore may suffer from chronic cutaneous lesions, or from infections with bacterial or protozoic agents. As example for a disease condition caused by a protozoic agent cutaneous leishmaniasis is to be named.

Cutaneous leishmaniasis (CL) is a vector born, mostly self-healing neglected tropical disease (NTD) predominantly endemic in poor (sub)tropical countries with bad sanitary and hygienic conditions, especially when these countries are war-torn. In the so-called "Old World" in Europe and the neighboring Middle Eastern Region, in contrast to the so called "New World", i. a. the Americas, with its own *Leishmania* species types the disease is mostly caused by the skin inoculation of the *L. major* or *L. tropica* parasite species through sand fly vector bites and is limited to skin manifestations without systemic disease symptoms (old world cutaneous leishmaniasis, OWCL). When female sand flies hosting the promastigotic form of leishmania parasites (pLPs) suck blood from humans the pLPs are taken up mostly by human macrophages, where they lose their flagella and change into amastigots (aLPs). Intracellular proliferation of aPLs invalidates macrophages as key effectors of immune defence and wound healing.

In CL endemic regions with 700,000 to 400,000 new cases every year according to WHO estimations the mainstream treatment approach actually consists in reducing the number of LPs in the infected tissue by applying topical formulations containing drugs, which have toxic effects on parasites, such as pentavalent antimony, fungicides, cancer toxics and others. If the CL lesions are too big, too numerous and at sites of the face, which are too painful to treat by intra-cutaneous injections into the CL lesion rim (lip, eye lid, nose, ear), a disease form named complex CL, systemic antimony injections are recommended in CL endemic countries. They have considerable side effects, requiring hospitalisations in countries, which can afford them.

None of these anti-protozoan drugs have a European drug license for CL. This is not astonishing, as CL mostly caused by *L. infantum* actually is quite rare in Europe and the indication of CL falls under the European Orphan Drug Act (less than 5 patients in 10,000 people). However, this could change as a great number of refugees from war-torn and poverty-stricken regions, where CL is endemic, are about to import the NTD CL to Europe, and phlebotomies have already been detected in parts of Middle Europe.

If so far commercially available prefabricated wound dressings, e.g. gauze, plaster and pre-fabricated films with and without hydrocolloids, are used for dressing of OWCL skin defects (Morizot et al, Travelers with cutaneous leishmaniasis cured without systemic therapy, Clin. Infect Dis 2013, 57 (3):370-380), this has several drawbacks: in poor countries such sterile dressings are either too expensive or unavailable, day to day renewals of aseptic dressing have to be applied by trained medics in leishmania centers, which requires additional manpower and makes the patients travel long distances to the sparsely distributed centers with CL treatment know-how.

Some of the commercially available dressings are non-adsorbent, have polyacrylic nature, as a rule close airtight and therefore are counter-indicated for super-infected wounds. Some-times as in DE 695 33 658 T2 they describe a gel, which is a moist jelly and therefore needs a fibrous support, sometimes as in WO 2015059501 they need a non-hydrogel backing layer. All these classical dressings are not needed for mostly dry or at least semi-dry CL lesions and do not fulfil the requirements of CL wound management in poor countries reducing the workload of the leishmaniasis medics by involving the patients into their own treatment wherever possible and by combining this with hand hygiene education propagated by the WHO. Consequently, there is an urgent need for alternative solutions.

Another type of lesion with increasing prevalence also in more developed countries are lesions due to actinic keratosis, in particular non-infectious lesions due to actinic keratosis. Actinic keratosis (AK) is a pre-cancerous thick, scaly, or crusty geriatric skin lesion, which is more common in fair-skinned people, who are frequently exposed to UV sunlight. Lesions due to actinic keratosis can have a range of appearances, for example thick, scaly, or crusty areas that often feel dry or rough, and in the early stages may first be recognized haptically rather than visually, as the texture of the skin is different from that of surrounding skin. In later stages the lesions often have an erythematous (red) base accompanied by ulceration, nodularity, or bleeding. Such AKs should be treated, because when left untreated they can turn into skin cancers (basaliomas, spinaliomas). Photodynamic therapy constitutes the most effective and esthetic treatment form. To increase the tissue content of reactive oxygen species (ROS) to micro-molar levels, which kill hyper proliferating epithelial cells, expensive photosensitizers are needed. Topical chemotherapy with 5-FU cream or physical cryotherapy are more economic treatment forms. However, chronic wounds can result from both local therapies, especially from 5-FU crème. In the Rotterdam study published in 2013 (Flohil SC1, van der Leest R J, Dowlatshahi E A, Hofman A, de Vries E, Nijsten T. Prevalence of actinic keratosis and its risk factors in the general population: the Rotterdam Study. J Invest Dermatol. 2013 August; 133 (8):1971-8. doi: 10.1038/jid.2013.134. Epub 2013 Mar. 19), the prevalence in bald elderly men was found 49%. Increasing prevalence also in developed countries might at least partly be due to increased travel activities to sun-rich regions of the world.

The objective of the invention is to provide a composition suitable for serving as a dressing for cutaneous lesions, in particular for leishmanial lesions and/or for lesions due to actinic keratosis, which can be easily handled and preferably does not necessarily require qualified medical personnel. The composition should also have superior effects in combating cutaneous lesions, in particular leishmania lesions in comparison with expensive drugs, which might have severe side-effects and bear the risk of increasing drug resistances, and should prevent new infections.

DESCRIPTION OF THE INVENTION

The composition for dressing cutaneous lesions, in particular leishmanial cutaneous lesions and/or lesions due to actinic keratosis, comprises—based on the total weight of the composition—the following ingredients: 10.0 weight percent to 35 weight percent, such as 15 to 30 weight percent, or 31 to 35 weight percent, of a one or more diols, selected from group comprising 1,2-propylene glycol, 1,2-pentanediol, 1,3-butanediol and 2,2'-[Ethane-1,2-diylbis(oxy)]di(ethan-1-ol). Furthermore, the composition comprises 2.0 weight percent to 20 weight percent, for example 2.5 to 15.0, such as 6.0 to 9.0 weight percent, of at least one first film-forming agent, selected from one or more of a cellulose derivative, hemicellulose, a hemicellulose derivative, chitosan, a chitosan derivative, or oligoglucosamines. The composition further-more comprises 0.2 to 25.0 weight percent, preferably 0.3 to 20.0 weight percent, of at least one second film-forming agent, selected from one or more thickening agents. Furthermore, the composition comprises 0.2 to 25.0 weight percent, preferably 0.3 to 20.0 weight percent, of one or more polymeric surfactants. Furthermore, the composition comprises 0.01 to 0.5 weight percent, preferably 0.07 to 1.1 weight percent chlorate-free chlorite. The remainder of the composition is water, thus resulting in a total of 100.0 weight percent. The composition is able to solidify after application onto a cutaneous lesion, such as a leishmanial cutaneous lesion or an actinic keratosis lesion, thus first constituting a flowable and afterwards a solid dressing.

The composition may comprise one of the aforementioned diols or any mixture of two or more of those diols. In the latter case the sum of diols contributes to the range of 10.0 weight percent to 35.0 weight percent. In a particular embodiment, the composition contains one diol, preferably 1,2-pentanediol. Due to the content of diol the composition is advantageously auto-sterile and thus can be prepared under non-sterile conditions without requiring additional sterilization, and enables a long shelf-life prior to use. 15 to 30 weight percent of a diol may be sufficient for ensuring auto-sterility, for example 22 to 30 weight percent, such as 23 to 30 weight percent, for example 23 to 27 weight percent, such as 25 weight percent. For compositions with increased demand with regard to auto-sterility 31 to 35 weight percent may be used. The diol content is for example 22 to 35 weight percent.

The composition contains 2.0 to 20.0 weight percent of at least one first film-forming agent, selected from one or more of a cellulose derivative, hemicellulose and/or a hemicellulose derivative. Consequently, the 2.0 to 20.0 weight percent of the first film-forming agent, such as 5.0 to 10.0 or 6.0 to 9.0 weight percent, may be constituted by one or more members, independently selected from cellulose derivatives, hemicellulose, hemicellulose derivatives, chitosan, a chitosan derivative, and/or oligoglucosamines. After the composition has solidified on a cutaneous lesion the at least one film-forming agent will increase the resistance to tearing forces, thus advantageously reducing the risk of cracks being formed in the composition after solidification. Those of skill in the art know cellulose derivatives or hemicellulose derivatives, chitosan, a chitosan derivative, or oligoglucosamines. Non-limiting examples thereof are acetylated, deacetylated, ethylated, methylated, propylated, hydroxyethylated, hydroxymethylated, hydroxpropylated, nitrated, oxidized, sulfonated, xanthogenated, cross-linked and/or copolymerized celluloses, hemicelluloses, chitosans and oligoglucosamines, wherein one or more groups of the respective celluloses, hemicelluloses, chitosans and oligoglucosamines, which are amenable to the modification, may be modified by the same or by different modifications. The modifications can extend to all modifiable groups, or alternatively can be partial modifications, thus for example resulting in celluloses or hemicelluloses, which are partially oxidized or have been subjected to one or more of the modifications described herein. Particular examples of chitosans or chitosan derivatives are those having a molecular weight not exceeding 100.000 g/mole, for example having a molecular weight in the range of 5.000 to 75.000 g/mole, such as 5.000 to 20.000 g/mole. Particular examples of oligo-glucosamines are those having a degree of polymerization of up to 30, up to 25, up to 20, up to 15, up to 10 or up to 5, for example a degree of polymerization in the range of 5 to 25, in the range of 7 to 20 in the range of 10 to 15. Preferred examples of cellulose derivatives are cellulose ethers. Special examples of first film-forming agents are hydroxypropylcellulose HPC (for example available as Hyprolose or Klucel®), or hydroxypropylmethylcellulose HPMC (for example available as Hypromellose, Pharmacoat®, Culminal®), preferably having a viscosity of 1-10 mPa·s, preferably 3-6 mPa·s, with average molecular weights between 95,000 and 850,000, preferably between 140,000 and 370,000, and preferably are added at concentrations between 2.5-15 weight percent, preferably 5-10 weight percent, such as 6-9 weight percent.

The composition furthermore comprises 0.2 to 25.0 weight percent of at least one elastic second film-forming agent, which is selected from one or more thickening agents. While the first film-forming agent confers tearing resistance to the composition after solidify-cation, a composition devoid of the at least one elastic second film-forming agent would be brittle and gradually splinter off from the cutaneous lesion due to movement of the underlying tissue. In a surprisingly found synergistic effect the elastic second film-forming agent cooperates with the at least one first film-forming agent, thus resulting in a composition, which after solidifying is not brittle but elastic enough to safely adhere to the surface of the cutaneous lesion and the surface of the surrounding skin despite the distortions of the surface due to movement of the underlying tissue.

The composition contains 0.005 to 0.5 weight percent, preferably 0.01 to 0.1 weight percent, such as 0.01 to 0.15 weight percent chlorate-free chlorite, for example IELC determined chlorite added as water solutions of the chlorate-free chlorite composition. The term "chlorite" refers to the anion $[ClO_2]^-$. The chlorite may for example be present in the form of sodium chlorite or another alkaline metal salt of chlorite. In the context used herein, chlorate-free chlorite is chlorite, which does not contain more than 1 mole percent chlorate, for example not more than 0.9 mole percent, not more than 0.8 mole percent or not more than 0.7 mole percent chlorate, preferably determined by IELC.

Methods of preparing chlorate-free chlorite are known to those of skill in the art. For example, chlorate-free chlorite can be obtained by expelling chlorine-free chlorine dioxide gas into a carbonate dioxide solution having a pH of 10.5, and then adding sodium peroxide granules to reduce remaining chloride dioxide to chlorite and oxygen, followed by removing precipitating bicarbonate. For example, the composition can comprise a chlorate-free chlorite composition dissolved in water, which may be prepared as described in example 1.

When preparing the chlorate-free chlorite composition according to example 1, the chlorate-free chlorite composition dissolved in water may contain chlorite, minor amounts of chloride and chlorate as well as the two peroxides, $Na_2CClO_6$ and $Na_2Cl_2O_6$, which form as peroxychlorate adducts. Apart from the aforementioned peroxides, the composition preferably does not contain any other peroxides, such as for example hydrogen peroxide, or contains less than 0.001 weight percent of other peroxides. The chlorite content of the chlorate-free chlorite composition dissolved in water can be analyzed either by photometry at 260 nm or by ion exchange liquid chromatography (IELC). The amount of the chlorate-free chlorite composition dissolved in water added is based on the IELC dosage of chlorite in g/g (molar mass of $NaClO_2/ClO_2^- = 90.44/67.45$ g·mol−1). In the IELC analysis, the chlorate-free compositions dissolved in water contain not more than 1.2 mol % of chloride and not more than 1 mol % of chlorate with respect to the molar IELC concentration of chlorite. In the IELC analysis, the peroxides, $Na_2CClO_6$ and $Na_2Cl_2O_6$, stable in solution but not stable as solids, are also contained in chlorate-free chlorite composition dissolved in water, which is thought to contribute to the oxidation of the first film-forming agent, and they decompose to chlorite on the IELC column. The sum of the molar content of peroxides is calculated as follows:

$$\Sigma moles(Na_2CClO_6 \text{ and } Na_2Cl_2O_6) = moles\ chlorite^{IELC} - moles\ chlorite^{260\ nm}$$

$$\Sigma moles(Na_2CClO_6 \text{ and } Na_2Cl_2O_6) \text{ can vary from 2 to 30 mol \% of molar chlorite}^{IELC}.$$

Accordingly, in one embodiment the chlorate-free chlorite can comprise the peroxide $Cl_2O_6^{2-}$, a desoxo-dimer of peroxochloric acid, or one of its salts, for example as sodium salt, $Na_2Cl_2O_6$, and/or can comprise $CClO_6^{2-}$, a carbon dioxide adduct of peroxochloric acid or one of its salts, for example a sodium salt, $Na_2CClO_6$, wherein the ratio of the peroxide or the carbon dioxide adduct, or the combined ratio of the peroxides and the carbon dioxide adduct, is in the range of 2 to 30 mole percent with respect to chlorite. Such a chlorate-free chlorite is obtainable by preparing chlorate-free chlorite as described herein.

The chlorate-free chlorite is advantageously better suited as a component of a composition for dressing leishmanial cutaneous lesions than chlorate-containing chlorite, because adverse effects of chlorate are minimized. The chlorite of the chlorate-free chlorite is helpful for oxidizing and thus cross-linking single molecule chains of the first film-forming agent, for example molecules of cellulose derivatives. Most of the oxidants used as chemical reagents for the industrial production of oxidized cellulose, such as chlorine, hydrogen peroxide, peracetic acid, chlorine dioxide, nitrogen dioxide, persulfates, dichromate-sulfuric acid, hypochlorous acid, hypohalites and a variety of metal catalysts cannot be used as oxidizing agents because of their toxicity and strong spontaneous oxidizing power. Surprisingly, it was found that chlorite, which is chlorate-free, can be used for a gentle biocompatible oxidation of the first film-forming agent, promoting a solidified layer. Without wishing to be bound by any theory it is assumed that the solidification is a result from both drying due to loss of water after the exposure of the composition to the environment and a cross-linking of molecules of cellulose derivatives, hemicelluloses and/or hemicellulose derivatives initiated by the oxidizing effect of chlorate-free chlorite. The solidified composition usually remains intact for at least 24 to 48 hours and can be easily refreshed in the quality by applying one new layer on top of the old one, for example in daily intervals, for at least 6 times. The application can, for example, be done using a sterile finger. At a neutral pH and above, the chlorite preparation has only very weak oxidizing properties, which advantageously guarantee a long shelf life of the composition. Fe-porphyrines are omnipresent in lesions and activate the chlorite preparation as oxidizers in the composition.

The composition is a flowable gel and can be described as staying liquid or semiliquid in a closed container, wherein the term "semiliquid" is used as normally understood by a person of skill in the art of Galenics, thus having characteristics in between solid and liquid compositions. In particular, semiliquid compositions are dimensionally stable but can be plastically deformed when being subjected to a sufficiently high force, for example when spreading the composition on the skin or the cutaneous lesion of a subject, which may for example be a human, a mammal or a non-mammal animal, and return to dimensional stability after removing the force.

While the composition keeps its flowable state in a closed container and immediately after removing from a container, thus enabling squeezing out or pouring out of the container and where applicable easy spreading over a lesion. Once removed from a container, the composition solidifies within approximately 2 to 30 minutes after application onto cutaneous lesion of a subject, thus forming a solid but flexible film. This film forms a barrier which protects the cutaneous lesion from contaminating and/or infecting agents from the environment. Advantageously, the layout also constitutes a mechanical barrier which is strong enough to prevent bites from insects such as sandflies, thus preventing super-infection with additional Leishmanial spec, when used with subjects endangered by possible insect bites. The composition is a gel and is essentially free or preferably completely free of fibrous substances. Due to the flowable, for example liquid or semiliquid nature of the composition it can be effectively applied onto a cutaneous lesion, for example a leishmanial lesion, and completely covers the lesion irrespective of a potentially irregularly shaped surface of the lesion, thus sealing it off from the outside environment. Likewise, due to the flowable nature of the composition, applying the composition onto the cutaneous lesion, which may include spreading the composition on the cutaneous lesion, advantageously does not require strong forces to be exerted, thus minimizing irritation of the cutaneous lesion. Contrary to conventional wound dressings, which comprise supports, such as flexible textiles, woven materials or sponge-like structures, and which—although being flexible—are still solid supports, any contact of which might irritate or injure the surface of the lesion, the composition described herein due to its initially flowable nature minimizes the danger of causing additional injuries or irritation of the surface of the lesion.

In summary, with the composition described herein a dressing for cutaneous lesions, such as leishmanial lesions and/or lesions due to actinic keratosis, is disclosed, which on the cutaneous lesion solidifies into a film, for example a thin film having a thickness of less than one millimeter, less than 0.5 mm or less than 0.2 mm. An oxidized first film-forming agent contributes to the tensile strength, and an elastic second film-forming agent contributes to the elasticity of the solidified lesion dressing. The solidified composition usually allows at least 24 hours of physical integrity of the resulting film protecting the lesion from adverse effects from the environment, or in context with leishmaniosis from new sand fly bites with parasite transfer to healthy subjects as well as from super-infecting pathogenic microorganisms. This film can be removed using water or an essentially water-based solvent, and allows regular gentle lesion cleansing until final physiological closure or healing of the cutaneous lesion. Consequently, the composition for dressing cutaneous lesions initially is in a flowable state, and when covering the cutaneous lesion and surrounding areas of skin subsequently solidifies into a film, which initially is a one-layered film, although by subsequent applications of the flowable composition onto the film, a multi-layered film can be created.

It has been surprisingly found that even in OWCL face lesions, which because of their size (more than 4 cm in diameter) or location (eye lid, nose, lips) could not be treated with either electrosurgical debridement of the cutaneous lesion nor with antimony chemotherapy, the use of a composition for dressing of leishmanial lesions, which has the special feature of forming an solid but flexible film on the lesions after minutes of application, promotes the healing of the leishmaniasis skin lesions and additionally even protects the lesions from sand fly bites and from super-infections. When free of colorants, the film is colorless and transparent, and thus virtually invisible on the cutaneous lesion.

The thickening agent may be selected from any biocompatible thickening agent known to the person of skill in the art, wherein the term "biocompatible" designates a substance, which does not cause adverse immunological or pharmaceutical reactions. Advantageously, the thickening agents confer elasticity to the composition after drying. Consequently, while the polysaccharides contribute to resistance against tearing forces, the thickening agent ensures that the drive composition is still flexible and will not crack due to a movement of the underlying cutaneous lesion or skin. In preferred embodiments, the thickening agent is selected from one or more of the group comprising gum Arabic, guar gum, tragacanth, damar gum, carrageenan, alginic acid, alginate, pectin, gelatin, polyvinylpyrrolidone, or derivatives thereof. Their weight percentage or combined weight percentage in the composition is 0.2 to 25.0 weight percent, preferably 0.3-20.0 weight percent, in particular 0.5 to 10 weight percent, such as 1.5 to 7.5 weight percent, for example 2.0 to 7.0 weight percent, e.g. 6.0 weight percent. Examples of polyvinylpyrrolidones (PVP) are available as Povidone, Plasdone® (Ashland Inc., USA) or Kollidone® (BASF, Germany), preferable in the molecular weight classes of K 12-K90.5-30. Because of their superior elasticity properties, some types of gelatin are also very suitable to replace natural gums. In case bovine gelatin is used it will be BSE-free for safety reasons. Pure pork gelatin may also be used, but must be avoided in case cultural or religious restrictions exist.

The polymeric surfactants can be any biocompatible substance known to the person of skill in the art. The polymeric surfactant contributes to improved adhesion of the composition to the skin and/or the cutaneous lesion to be covered by the composition, both before and after solidification, by mediating contact to any lipophilic substance present on these surfaces. The molecular size of the surfactant preferably is high enough to prevent absorption, which in turn would promote hemolysis, for example at least 1000, for example at least 8000. According to a particular embodiment the polymeric surfactant is selected of one or more of the group comprising poloxameres and sugar tensides. Non-limiting examples are alkyl polyglycosides, polysorbates and sucrose esters. Special examples of polymeric surfactants are poloxameres, available as Kolliphore® (BASF, Germany) or Pluronic® (BASF, Germany), or polysorbates, available as Tween 20, Tween 60 or Tween 80.

The composition may optionally comprise at least one additional ingredient, independently selected from one or more organic solvents, plasticizers, solubilizers, preserving agents, antiseptically, antiparasitically, antibacterially, immunologically, metabolically and/or pharmaceutically active ingredients, insect repellents, colorants, such as dyes or pigments, and UV-blocking agents. Non-limiting examples for antiparasitic ingredients are in particular anti-protozoan ingredients, preferably anti-parasitic antibodies or ingredients acting against leishmania, such as pentadimine, meglumine antimoniate, sodium stibogluconate, miltefosine, allopurinol, preferably poly(hexamethylene) biguanide hydrochloride (PHMB), pentamidine, amphotericin-B, meglumine antimoniate, sodium stibogluconate, miltefosine, allopurinol, or artemisinine. Non-limiting examples for antibodies are in particular anti-protozoan antibodies and anti-cytokine antibodies, more preferably anti-leishmanial and anti-IL17 antibodies. Non-limiting examples for anti-bacterially active ingredients are antibiotics such as β-lactames, glycopeptides, aminoglyocosides, polypeptide antibiotics, chinolones or sulphonamides. Non-limiting examples for immunologically active ingredients are anti-inflammatory or immune-modulating ingredients, such as e. g. non-steroidal anti-inflammatory [NSAIDs], bio-activated reactive oxygen species [ROS], cytokines). The composition preferably is free of compounds, which are not admissible for application onto lesions, such as antiseptics or preservatives for which, depending on the respective applying laws, concerns exist, for example boric acid or thiomersal. Colorants may be added for example in order to optically cover the lesion by conferring a colour to the composition and ultimately to the solidified film, which is similar or identical to the skin surrounding the cutaneous lesion. UV blocking agents can be comprised in the composition in order to prevent or minimize damage of the cutaneous lesion surface by ultraviolet radiation. UV filtering agents can be comprised in the composition in order to transmit UV-A light wave lengths which are needed for ROS activation in chlorate-free produced chlorite and to protect cutaneous lesions from non-desired damaging UV radiation. According to a particular embodiment the pharmaceutically active components are selected from nonionic and/or cationic compounds, preferably in combination with hydroxypropylcellulose.

In the composition, up to 50 volume percent of the water may be replaced by isopropyl alcohol, in which case the amount of water used for completing the 100.0 weight percent may refer to a mixture comprising up to 50 percent of isopropyl alcohol, for example up to 40 percent, up to 30 percent, up to 20 percent or up to 10 percent. The inclusion of isopropyl alcohol advantageously allows a better inclusion of lipophilic ingredients, such as for example pharmaceutical ingredients in comparison to water alone.

The viscosity of the composition should be low enough to enable a gentle application and, where necessary, a thin spreading and uniform distribution of the composition onto the lesion, such as a leishmanial lesion and/or lesions due to actinic keratosis, and for example should not exceed $2\times10^4$ Pa·s, in particular should not exceed $10^4$ Pa·s. In a particular embodiment the viscosity of the composition is in the range of 1 Pa·s to $2\times10^4$ Pa·s, such as 1 Pa·s to $10^4$ Pa·s, 1 Pa·s to $10^3$ Pa·s, 1 Pa·s to $5\times10^2$ Pa·s, 2 to 100 Pa·s, or 3 to 60 Pa·s, in particular 10 to 20 Pa·s, such as 5 to 15 Pa·s or 8 to 12 Pa·s, when measured at a temperature of 25° C. in a rotational viscosimeter at a shear rate of $10^{-1}$ s after reaching stable values, which may take up to 8 days. For example, a rotational rheometer can be used (for example a Kinexus rotational rheometer, Malvern Instruments Ltd.) with a cone and plate geometry (40 mm, 4°) at 25.0 degrees ° C., in shear rate range from 0.1 up to 100 1/s. Shear rates above 100 1/s are not practicable, as the gel might fling from the gap. A preferred shear rate of 0.1 1/s.

Compositions having such a viscosity advantageously can be easily applied onto a cutaneous lesion and the surrounding skin area while still being viscous enough not to autonomously spread in an uncontrolled and undesired manner before solidifying by drying and/or crosslinking of the molecules of the first film-forming agent. It is also clear to those of skill in the art that upon prolonged storage the viscosity of the composition may slightly change by ±25%, such as by ±20% with respect to the original value determined after preparing the composition.

The composition is useful as a take-away dressing to be provided to subjects suffering from cutaneous lesions, for example lesions due to leishmaniasis. It does not require sterilization because of its content of diol, preferably propylene glycol. It can be packed in small suitable closed containers, such as tubes or syringes.

The composition described herein is useful for the treatment of a cutaneous lesion by applying a layer of the composition onto the lesion and allowing the composition to solidify into a film. As already described, the film is solid but flexible, and covers and protects the underlying cutaneous lesion, and preferably also regions of intact skin immediately neighboring the cutaneous lesion.

In the context of a composition for use in the treatment of a cutaneous lesion, prior to applying a layer onto the cutaneous lesion, the cutaneous lesion may be debrided and/or disinfected. Methods for debridement and disinfection are known to those skilled in the art, and non-limiting examples of debridement comprise autolytic, chemical, enzymatic, maggot, or surgical debridement, or physical debridement such as ultrasound debridement of high frequency electrosurgical cauterization. Debridement may for example be performed with surgery, bi-polar electro-surgery or with easy-to-regulate high frequent ultrasound.

The composition described herein is further useful for use in the treatment of a cutaneous lesion, wherein after a previous application of a layer an additional layer of the composition is applied onto the previously applied, solidified layer and the additional layer is allowed to solidify, and wherein the application of an additional layer of the composition optionally is repeated one or several times, for example one to twelve times, such as seven times. Preferably, each layer is allowed to protect the cutaneous lesion over a time period which does not exceed the period during which the layer is expected to stay intact, and after that period the film on the cutaneous lesion is additionally enforced by applying a new layer onto the film, which solidifies, thus resulting in a film comprising one additional solidified layer. One embodiment comprises after a previous application of a layer of the composition applying one additional layer of the composition onto the previously applied, solidified layer, preferably within 12 to 60 hours, preferably within 18 to 30 hours, especially within 22 to 26 hours, such as 23 to 25 hours, for example 24 hours, and allowing the additional layer to solidify, and optionally comprises repeating the step of applying at one additional layer onto the previously applied and solidified layer, again within the previously described periods of time. The step of applying one additional layer onto the previously applied and solidified layer can preferably be repeated up to 12 times, for example 6 two 8 times, such as 7 times.

Each layer of the composition for use in the treatment of cutaneous lesions may preferably be applied using a disinfected means, thus reducing the risk of additionally infecting the cutaneous lesion. The means may be a spatula, a spoon or a stick. In a preferred embodiment the means is a disinfected finger, preferably a disinfected finger of the subject suffering from the cutaneous lesion. When subjects suffering from cutaneous lesions are enabled to apply the composition by themselves, the healthcare provided is substantially simplified because neither trained medical personnel travelling to the subject nor the subject travelling to a healthcare spot are required. To the contrary, the subjects can treat their lesions on their own and possibly only require a brief initial training about disinfecting the fingers and about applying the composition onto the cutaneous lesions. With no necessity to travel to healthcare spots or to wait for medical personnel travelling to the subjects, the compliance of the subjects can be largely increased, thus improving the chances of a successful disappearance of the cutaneous lesion even in geographical regions having less developed healthcare systems.

The composition for use in the treatment of cutaneous lesions as described herein may be used in a treatment cycle, wherein a treatment cycle comprises applying a new layer in intervals of 12 to 48 hours, in particular 20 to 28 hours, for a duration of 5 to 12 days, such as for a duration of 6 to 8 days, in particular 7 days, in the latter case resulting in a weekly treatment cycle. The treatment cycle may also allow one or two subsequent days where in the composition for use in the treatment is not applied to the cutaneous lesion. Preferably, one treatment cycle comprises applying a new layer once a day, for example once every 24±5 hours, such as once every 24±3 hours, once every 24±2 hours or once every 24±1 hour. After the completion of the treatment cycles the film comprising the solidified layers may be removed, and optionally a new treatment or a new treatment cycle is started in case the cutaneous lesion still exists. Consequently, after a certain period of time, during which underlying cutaneous lesion has been covered by the film and has not been disturbed by removing the film, the resulting thick film now consisting of many solidified layers is removed and replaced by a fresh and thin film. Where deemed necessary, the cutaneous lesion may optionally be disinfected before starting a new treatment or treatment cycle. Removing the film may be performed by applying water, or water containing a tenside, a water-based disinfectant solution, such as sterile solution containing 0.1% of polyhexanide and 0.1% undeclylenamidopropylbetaine, or by applying high-frequency ultrasound. For example, using a solution enhanced by surfactants of the betaïne type, a film used to cover a leishmanial cutaneous lesion of a subject can be taken off by trained medics in leishmania centers after one week or even by the subject himself, after which the treatment of treatment cycles are continued as long as it takes to close the cutaneous lesion completely. The weekly or nearly weekly treatment cycle is repeated until the cutaneous lesion ultimately disappears. The treatment cycle may also be nearly weekly by for example lasting less or more than seven days, and may also include one or two subsequent days were in no treatment occurs. In case of leishmanial cutaneous lesions, for example an application of the composition in weekly intervals and in average for a duration of 7 weeks in a cutaneous leishmaniasis point of care of non-hospitalized subjects, or by subjects themselves without even accessing a point of care, has a considerable advantage versus the so far WHO recommended chemotherapy with pentavalent antimony, which may need up to 21 interventions with inpatient treatment.

The composition described herein may, however, be used in context with any cutaneous lesion. Non-limiting examples of lesions are those selected from the group comprising cutaneous lesions due to parasitic infections, in particular leishmanial cutaneous lesions; cutaneous lesions due to bacterial infections; cutaneous diabetic lesions; cutaneous lesions due to xerosis, pruritus, cutaneous lesions due to eczematous dermatitis, cutaneous lesions due to stasis dermatitis, cutaneous lesions due to chronic venous insufficiency; cutaneous lesions due to geriatric skin, in particular cutaneous lesions due to actinic keratosis; light-induced cutaneous lesions, in particular actinic keratosis; cutaneous lesions related to transplantation wounds; and cutaneous lesions related to ulcus cruris. The lesions related to geriatric skin may in particular be those in context with xerosis, pruritus, eczematous dermatitis, and/or chronic venous insufficiency, but are not necessarily related to those conditions. According to one particular embodiment the cutaneous lesion is a leishmanial cutaneous lesion, or a leishmanial cutaneous lesion of a diabetic subject, and/or a cutaneous lesion of a subject suffering from geriatric skin, in particular due to actinic keratosis. As will be understood by medical practitioners, actinic keratosis is generally considered as a condition of geriatric skin, owing to the fact, that over the lifetime of a person damage due to accumulated light exposure, in particular exposure to UV radiation, may with an increased probability lead manifestation of actinic keratosis in old age. However, it will also be understood that even younger subjects may suffer from actinic keratosis, in particular subjects living in regions of high solar intensity or subjects exposed to solar radiation, for example due to frequent work outside of buildings, close to the sea or in high altitudes. The composition described herein is useful in context with all cutaneous lesions mentioned herein. As will be shown in the examples hereinafter, exemplary positive results were obtained when applying the composition to cutaneous leishmanial lesions, even those aggravated by Type II diabetes. Furthermore, positive results were also obtained when applying the composition to cutaneous lesions due to actinic keratosis, which had not even been treated with usual first-line therapies usually applied for actinic keratosis.

The invention also relates to a method of treatment of a cutaneous lesion, comprising applying a layer of the composition as described herein onto the cutaneious lesion and allowing the composition to solidify into a film. Optionally the method may comprise debriding and/or disinfecting the cutaneous lesion prior to applying the layer of the composition. In one embodiment the method comprises, after a previous application of a layer, the application of an additional layer of the composition onto the previously applied, solidified layer and allowing the additional layer is to solidify, and optionally repeating the application of an additional layer of the composition one or several times, for example one to twelve times, such as seven times. Applying each layer of the composition may be done by using a disinfected means, for example a spatula, a spoon or a stick, or a disinfected finger, preferably a disinfected finger of the subject suffering from the cutaneous lesion. The treatment method may involve a treatment cycle, wherein the treatment cycle comprises applying a new layer in intervals of 12 to 48 hours, in particular 20 to 28 hours, for a duration of 5 to 12 days, in particular 7 days. After a completion of the treatment cycle the method may further comprise removing the solidified layers and optionally starting a new treatment or treatment cycle in case the cutaneous lesion still exists. Reference is also made of disclosures made elsewhere herein.

The invention also relates to a composition as described herein for use in the treatment of a cutaneous lesion, wherein the cutaneous lesion is selected from the group comprising cutaneous lesions due to parasitic infections, in particular leishmanial cutaneous lesions; cutaneous lesions due to bacterial infections; cutaneous diabetic lesions; cutaneous lesions due to xerosis, cutaneous lesion due to pruritus, cutaneous lesions due to eczematous dermatitis, cutaneous lesions due to stasis dermatitis, cutaneous lesions due to chronic venous insufficiency; cutaneous lesions due to geriatric skin, in particular cutaneous lesions due to actinic keratosis; light-induced cutaneous lesions, in particular actinic keratosis; cutaneous lesions related to transplantation wounds; and cutaneous lesions related to ulcus cruris. The composition for use in the treatment may according to one embodiment be free of antiparasitically, antibacterially, immunologically, metabolically and/or pharmaceutically active ingredients, thus owing its efficacy solely to the remaining ingredients of the composition. According to another embodiment the composition may contain one or more ingredients, selected from the group consisting of antiparasitically, antibacterially, immunologically, metabolically and/or pharmaceutically active ingredients. The invention also relates to a method for the treatment of a cutaneous lesion, wherein the cutaneous lesion is selected from the group comprising cutaneous lesions due to parasitic infections, in particular leishmanial cutaneous lesions; cutaneous lesions due to bacterial infections; cutaneous diabetic lesions; cutaneous lesions due to xerosis, cutaneous lesion due to pruritus, cutaneous lesions due to eczematous dermatitis, cutaneous lesions due to stasis dermatitis, cutaneous lesions due to chronic venous insufficiency; cutaneous lesions due to geriatric skin, in particular cutaneous lesions due to actinic keratosis; light-induced cutaneous lesions, in particular actinic keratosis; light-induced cutaneous lesions, cutaneous lesions related to transplantation wounds; and cutaneous lesions related to ulcus cruris.

The invention further relates to a method for preparing a composition as described herein, comprising the following steps: transferring the at least one diol into a chamber suitable for vacuum stirring; covering the diol with the at least one first film-forming agent, the at least one second film-forming agent and that at least one surfactant; adding water containing the chlorite; stirring the content of the chamber under reduced pressure, removing the stirred content from the chamber. The stirring under reduced pressure is preferably performed between 0.5 to 5.0 min, for example for about 1.5 min. The reduced pressure preferably is in the range of 0.05 to 0.5 hPa, preferably 0.1 hPa. The method is in particular suitable for mixing the first film-forming agent without formation of clumps. Using high-power mixers, the respective components of the composition may alternatively be added simultaneously or with no particular sequence while still sufficiently avoiding clump formation.

In summary, the composition described herein is useful for protection of subjects suffering from cutaneous lesions. Pilot experiments were done with subjects suffering from leishmanial cutaneous lesions and showed protection of those leishmanial cutaneous lesions from noxious external influences due to super-infecting microbes. After careful hand disinfection with alcohol-based hand-rub as recommended by WHO, the subject puts 1 to 3 drops of the composition on the tip of his now aseptic finger gently dispersing the gel on the lesion and surrounding intact skin, 0.5 cm beyond of the lesion border. Surprisingly, the pilot field experiments also showed that the intact film protects against bites of sandflies propagating *L. tropica* parasite species, thus keeps sandflies from biting lesions and sucking blood from infected subjects, which in subsequent bites could be transferred to healthy subjects.

The invention further relates to a container, comprising in one compartment a composition as described herein. The container can have a suitable means to be opened, for example a screw cap, or can have a means for releasing a defined amount of the composition, wherein the means may optionally be a sterile means also suitable for spreading the composition on the cutaneous lesion. Corresponding means are well known to those of skill in the art and in view of the disclosure made herein can be easily selected appropriately. According to one embodiment, the container is a package unit or dispenser, for dispenser releasing a predetermined amount of the composition. For example, the package unit contains an amount of the composition, which is sufficient for covering one cutaneous lesion, for example one leishmanial cutaneous lesion, and may for example be sufficient to cover a cutaneous lesion of an average size of 20 to 80 square centimeters. Alternatively, the package unit contains an amount of the composition, which is sufficient for repeated daily applications of the composition onto a lesion over a period of one week, two weeks or three weeks.

In a further embodiment, the container may comprise at least one additional compartment containing either a solution for removing a film from a skin or a cutaneous lesion, or a disinfectant, or wherein the container comprises two additional compartments, wherein one compartment comprises a solution for removing a film and a second compartment comprises a disinfectant. Disinfectants are known to those skilled in the art. A sterile solution containing 0.1% of polyhexanide and 0.1% undeclylenamidopropylbetaine is an example of a solution which can serve both for disinfection and for removing the film.

In a further aspect, the invention relates to a kit, comprising a composition as described herein, for example presented in a container as described herein, and optionally in addition comprising a disinfectant and/or a solution for removing a film, and/or a means for applying the composition onto a cutaneous lesion.

The invention also relates to a film, comprising at least one solidified layer of a composition as described herein.

EXAMPLES

The invention will further be illustrated in the following examples, which are by no means are to be construed as limiting the invention.

Example 1: Production of Chlorate-Free Chlorite From Chlorine Dioxide

The production of chlorine ($Cl_2$) free chlorine dioxide gas is well known to an expert in this field. The process of producing chlorate free (<1 mol % of the molar chlorite concentration is chlorate) consists of introducing chlorine-free chlorine dioxide gas into an alkaline (pH 8 to pH 10) peroxide containing solution. The preferable process is known from U.S. Pat. No. 3,123,529, where it is described as a procedure to stabilize chlorine dioxide, because through a chemical reaction of .ClO2 with carbonate peroxide ($2Na_2CO_3.3H_2O_2$), which is water soluble up to 13 g %, the solution absorbs the 20 fold amount of the chlorine dioxide gas in comparison to its physical solubility (2,900 ppm). In contrast to chlorite which has to be strongly acidified (pH <2) to release chlorine dioxide, a major amount of .$ClO_2$ is released again at low proton concentrations of a pH <7 to >5 the slightly acidic pH of the skin. To guarantee a shelf life of three years, the final solution should have a pH from 10 to 12 and should be kept in the dark. To obtain a chlorite solution, which is not only virtually free of chloride using chlorine free chlorine dioxide gas but also of chlorate the following procedure was chosen:

1. 30 g of carbonate peroxide ($2 Na_2CO_3.3H_2O_2$) are dissolved in 1 liter of demineralized sterile water.
2. Chlorine-gas-free chlorine dioxide gas is freshly produced from sodium chlorite and sodium peroxydisulfate to be physically dissolved in ultra-pure water (43 mM).
3. Over a period of 17-24 hours, 1 mole of chlorine dioxide gas is expelled with nitrogen gas from a chlorine-free chlorine dioxide solution at room temperature into one liter of a percarbonate [$2Na_2CO_3.3H_2O_2$] solution with the initial pH of 8.5 mounting to 10.5 when all chlorine dioxide has been absorbed.
4. The reaction starts with 50 g of percarbonate dissolved in 1 Liter of pure water which has pharmaceutical quality. 4×20 g of additional percarbonate are stepwise added, each time the yellowish Gordon complex of chlorite and chlorine ($Cl_2O_4^{(-1)}$) dioxide starts to form, until a final amount of 130 g percarbonate per liter (0.41 M) has been reached. A few solid sodium peroxide granules are finally added to destroy eventually remaining chlorine dioxide, which might not have reacted, until the final solution shows a pH of app. 12.
5. When all chlorine dioxide has been absorbed in the finished preparation, IELC analysis [instrument: Thermo Scientific™; mobile phase: 2.4 mmol/L $Na_2CO_3$/0.8 mmol/L $NaHCO_3$, stationary phase: Dionex™ IonPac AG23 (2×50 mm) IonPac AS23 (2'250 mm)] is used to determine the concentration of chlorite, and the impurities of chloride, chlorate and sulphate. The chloride impurity stems from the eventual chlorine gas impurity in the chlorine dioxide gas, the sulphate impurity stems from the peroxide used for the synthesis of chlorate-poor chlorite. The chlorite content is additionally measured photometrically at 260 nm in the final preparation.
6. This value is always lower than the IELC determined concentration of chlorite, as the adduct of peroxychlorate of $CO_2$ or of $HOCO_3^{(-1)}$ decomposes to chlorite bicarbonate and oxygen. The molar difference between both values chlorite$^{IELC}$-chlorite$^{260\ nm}$ is a measure for the peroxychlorate $CO_2$/$HOCO3^{(-1)}$ adduct described in WO 2000/048940. It may, for example, vary between 2 to 30 mole percent.
7. Following the above described procedure the amount of chloride and chlorate is kept at <1.2 mol % and <1% respectively] of the molar concentration of IELC determined chlorite concentration.
8. The total amount of chlorine absorbed as chlorine dioxide gas corresponds to the sum of chlorite, chloride and chlorate determined by IELC.

The solution is left standing in the dark in a closed glass vessel at room temperature. After 4 weeks, the degassing of $CO_2$ gas and the bicarbonate deposit formation have come to an end and the solution is cleared by filtration. During this time the peroxychlorate $CO_2$/$HOCO_3$ slowly forms the adduct with chlorite [$Na_2Cl_2O_6$], which is also described in WO 2000/048940. The chlorite adduct is also a potent oxidant, which is more stable than the bicarbonate/carbon dioxide adduct.

Example 2

250 g of 1,2 Propyleneglycol (EU pharmacopeia quality) were transferred to the chamber of a mixer for semi-solid formulations to be stirred under vacuum and the surface was covered with:
60.0 g of Hydroxypropylcellulose (Klucel GF)
6.0 g of Gummi Arabicum (Efficacia XE) and
6.0 g of Kolliphor407.

678.0 g of sterile water were added, which contained 10 g of a 9% (as measured by ion exchange liquid chromatography) solution of sodium chlorite produced in a chlorate-free manner. The mixer container was closed and stirred for 1.5 minutes at the setting 5 under a vacuum of 100 mbar. The composition obtained as a gel was then transferred to sterile calibrated containers or tubes to be finally used by subjects suffering from cutaneous lesions.

Example 3

250 g of 1,2-propylene glycol (EU pharmacopeia quality) were transferred to the chamber of a mixer for semi-solid formulations to be stirred under vacuum and the surface was covered with:
60.0 g of Hydroxypropylcellulose (Klucel GF)
10.0 g of Gelatine Type B dissolved in 16 g of sterile water at 500 C and
10.0 g of Kolliphor 407.
664.0 g of sterile water were added, which contained 10 g of a 9% solution of sodium chlorite produced in a chlorate free manner. The mixer container was closed and stirred for 1.5 minutes at the setting 5 under a vacuum of 100 mbar. The composition obtained as a gel was then transferred to sterile calibrated containers or tubes to be finally used by the subjects suffering from cutaneous lesions.

Example 4

45 cutaneous lesions in the ulcer stage resulting from *L major* skin infections of 31 subjects as proven by PCR, which according to WHO recommendations should have been due for in-hospital treatment with daily intramuscular infections of pentavalent antimony, were daily dressed as follows:

The cutaneous lesions were cleaned with a sterile solution containing 0.1% of polyhexanide and 0.1% undeclylenamidopropyl betaine. 1-3 drops of a composition prepared according to Example 2 put on a disinfected finger under aseptic conditions were gently dispersed on the lesions covering also 0.5 cm of the surrounding intact skin, which solidified into a thin transparent film after 15 to 30 minutes. This procedure was repeated daily by adding one new layer on top of the solidified old one. After 1 week the film consisting of several layers was dissolved by putting wet gauze soaked with a 0.1% solution of the disinfectant polyhexanide and the surfactant undeclylenamidopropyl betaine for 10 to 15 minutes on the lesions before restarting the weekly treatment cycle as long as it took for disappearance of the cutaneous lesions.

The median time for disappearance of the cutaneous lesions was found to be four weeks, the longest time was found to be 10 weeks. All OWCL lesions healed without systemic chemotherapy which would have required pentavalent antimony.

The result of this test is compared with the results of a previous study which has been published as "Stahl et al., "A randomized controlled phase II wound healing trial of cutaneous leishmanial ulcers with 0.045% pharmaceutical chlorite (DAC N-055) with and without bipolar high-frequency electro-cauterization versus intralesional antimony in Afghanistan", BMC Infectious Diseases 2014, 14:619.

Trial 1 as described hereinafter in Table 1 corresponds to protocol (1) of Stahl et al., i.e. intradermal injection of 0.6 ml sodium stilbogluconate.

Trial 2 as described hereinafter in Table 1 corresponds to protocol (3) of Stahl et al., i.e. wound dressing with 0.045% DAG N-055.

Trial 3 as described hereinafter in Table 1 corresponds to protocol (2) of Stahl et al., i.e. wound debridement followed by wound dressing with 0.045% DAG N-055.

Trial 4 is described hereinafter Table 1 corresponds to a dressing using the composition described herein.

Table 1 describes the median healing times in weeks:

| Description | Trial number | Median healing time [weeks] |
| --- | --- | --- |
| sodium stilbogluconate | Trial 1 | 9 |
| moist wound care (MWC) | Trial 2 | 7.3 |
| Debridement + MWC | Trial 3 | 4.9 |
| composition | Trial 4 | 4 |

It is evident from the results that the composition described herein (Trial4) leads to the shortest healing time of all 4 protocols (topical chemotherapy with $Sb^{(V)}$ in Trial 1, moist wound treatment after aggressive topical debridement under local anesthesia in Trial 3, moist wound treatment with basic amphiphilic crème alone in Trial 2 and Trial 4 with the composition described herein). Trial 4 comprised cases with complex leishmaniasis lesions, which could not be treated topically but which under normal circumstances would have required systemic $Sb^{(V)}$ chemotherapy. This risky systemic Sb(V) chemotherapy could be completely avoided. Moreover, the treatment of the protocol to be used with the composition (Trial 4) was performed by the CL patients on their own on 6 days of a week. The health care centers had to intervene only once a week for lesion cleansing with physiological saline before starting another weekly treatment cycle until final lesion healing.

Figure 1:
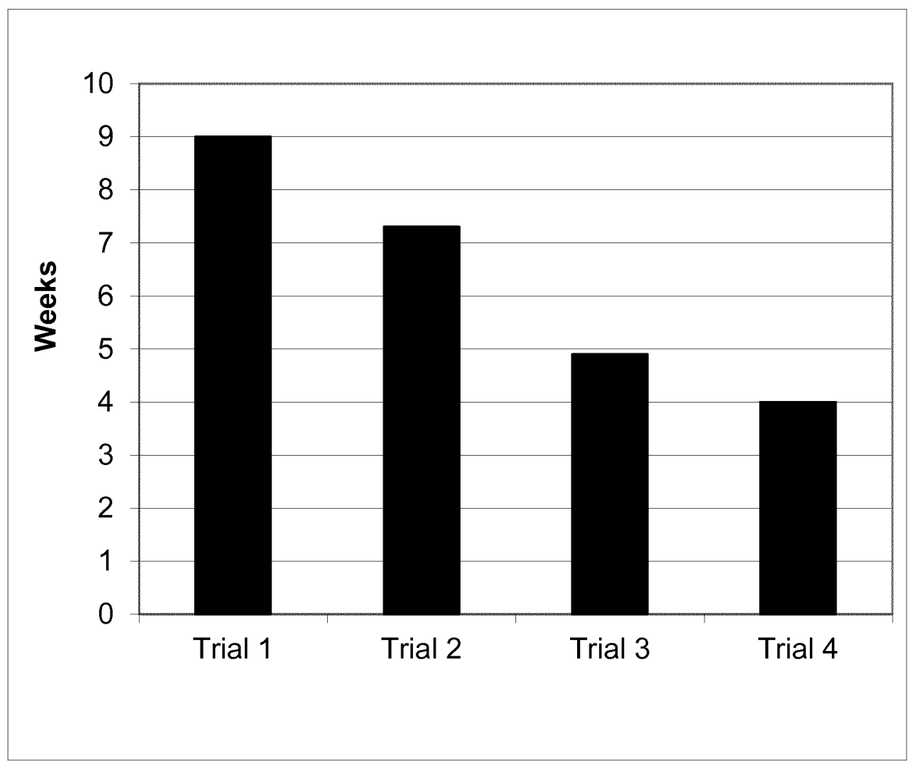
FIG. 1 shows the result of various means of treatment of cutaneous lesions.

The results of Table 1 are also visualized in FIG. 1.

Example 5

The composition prepared according to example 2 was also applied to cutaneous leishmania lesions of elderly subjects, whose lesion healing was complicated by their primary disease, diabetes type II. Also in such cases the composition was able to promote healing of their leishmanial cutaneous lesions, without treating them without pentavalent antimony ($Sb^V$), which would have had to be administered systemically by 21 systemic i.m. injections of $Sb^V$. Consequently, the subjects were spared the toxic side effects of this chemotherapy.

Example 6

The human patient was a fair-skinned male, 78 years of age. The patient had presented actinic keratosis for more than 15 years, with four excised basilomas on the face and one spinalioma in his face and on his bald head, which had been excised approximately four years earlier. Approximately three months prior to the treatment described herein, the patient had presented another temporal lesion due to actinic keratosis. The dermatologist treated him with diclofenac crème first, and in the absence of any improvement switched to a topical treatment 5-FU crème then. 5-FU crème worsened the wound situation and inflammation of the surrounding tissue. The lesion having a diameter of 4 cm was then dressed with the composition according to example 3. The inflammatory reaction already regressed after 3 days, complete aesthetic healing was achieved after 3 weeks.

Example 7

A fair-skinned bald human patient, 80 years of age, suffering from psoriasis for over 50 years and being under cortisone treatment because of giant cell arteritis for five years, had suffered from actinic keratosis for more than 10 years. Over a period of four weeks the patient daily once per day dressed his lesions after daily showers. After four weeks an excellent aesthetic healing of the lesions was noticed.

While in the preceding description and examples exemplary embodiments have been disclosed, it is obvious that a multitude of possibilities for variations exist. It is emphasized that exemplary embodiments merely constitute examples, which are not to be seen as limiting the scope, the ways of using or of configuring the invention. While the preceding description enables those of skill in the art to put the exemplary embodiments into practice, based on the disclosure of the inventive idea presented herein those of skill in the art are able to apply various modifications without leaving the scope of protection as defined by the claims although legal equivalents, such as more detailed disclosures in the description.

INDUSTRIAL APPLICABILITY

The composition described herein is useful as a means for treatment of cutaneous lesions.

The invention claimed is:

1. A film-forming composition for dressing cutaneous lesions comprising, based on the total weight of the composition:
   10.0 weight percent to 35 weight percent of one or more diols, that are 1,2-propylene glycol, 1,2-pentanediol, 1,3-butanediol or 2,2'[Ethane-1,2-diylbis(oxy)]di(ethan-1-ol),
   5.0 weight percent to 10.0 weight percent of at least one first film-forming agent, selected from one or more of a cellulose derivative, hemicellulose, a hemicellulose derivative, chitosan, a chitosan derivative, oligoglucosamine or oligoglucosamine derivative, the derivative being a modification by one or more of being acetylated, deacetylated, ethylated, methylated, propylated, hydroxyethylated, hydroxymethylated, hydroxpropylated, nitrated, oxidized, sulfonated, xanthogenated, cross-linked and/or copolymerized celluloses, hemicelluloses, chitosans and oligoglucosamines,
   0.2 to 25.0 weight percent of at least one elastic second film-forming agent, selected from one or more thickening agents,
   0.2 to 25.0 weight percent of one or more polymeric surfactants,
   0.005 to 0.5 weight percent chlorate-free chlorite, wherein the amount is effective to provide cross-linking of single molecule chains of the first film-forming agent
   an amount of solvent that is water or water and isopropyl alcohol, adding up to 100.0 weight percent of the composition, wherein isopropyl alcohol in the solvent is present in an amount of up to 50% of the solvent,
   wherein the film-forming composition converts from a flowable form to a solid but flexible film after removal from a closed container and application to the lesion.

2. The composition according to claim 1, wherein the one or more thickening agents is/are gum Arabic, guar gum, tragacanth, damar gum, carrageenan, alginic acid, alginate, pectin, gelatin, or polyvinylpyrrolidone, or derivatives thereof.

3. The composition according to claim 1, wherein the one or more polymeric surfactants is/are poloxameres or sugar tensides.

4. The composition according to claim 1, further comprising at least one additional ingredient, independently selected from organic solvents, plasticizers, solubilizers, preserving agents, antiseptically, antibacterially, immunologically, metabolically and/or pharmaceutically active ingredients.

5. The composition according to claim 1, wherein up to 50 percent of the water are replaced by isopropyl alcohol.

6. The composition according to claim 1, wherein the composition in a closed container has a viscosity in the range of 1 to $2 \times 10^4$ Pa·s, when measured at a temperature of 25° C.

7. A method of treating the cutaneous lesion wherein a layer of the composition of claim 1 is applied to the lesion and solidifies into a film layer.

8. The method of treating according to claim 7, wherein prior to applying the layer the cutaneous lesion is debrided and/or disinfected.

9. The method of treating according to claim 7, comprising after a previous application of the layer an additional layer of the composition is applied onto the previously applied and solidified film layer and the additional layer is allowed to solidify into a second film layer.

10. The method of treating according to claim 7, wherein the layer of the composition is applied using a disinfected means.

11. The method of treating according to claim 7, wherein a treatment cycle comprises applying a new layer in intervals of 12 to 48 hours, for a duration of 5 to 12 days.

12. The method of treating according to claim 11, comprising, after completion of said treatment cycle, the film layer comprising the solidified layers is removed, and, if the cutaneous lesion still exists, applying a new layer to initiate a new treatment cycle.

13. The method of claim 7, wherein the cutaneous lesion treated is selected from the group consisting of cutaneous lesions due to parasitic infections; cutaneous lesions due to bacterial infections; cutaneous diabetic lesions; cutaneous lesions due to xerosis, cutaneous lesions due to pruritus, cutaneous lesions due to eczematous dermatitis, cutaneous lesions due to stasis dermatitis, cutaneous lesions due to chronic venous insufficiency; cutaneous lesions due to geriatric skin, light-induced cutaneous lesion; cutaneous lesions related to transplantation wounds; or cutaneous lesions related to ulcus cruris.

14. The method of claim 7, wherein the cutaneous lesion is selected from the group consisting of leishmanial cutaneous lesions; cutaneous lesions due to actinic keratosis; and actinic keratosis.

15. Container, comprising in one compartment the composition according to claim 1.

16. Container according to claim 15, wherein the container is a package unit or dispenser.

17. Container according to claim 15, wherein the container comprises at least one additional compartment containing either a solution for removing the cutaneous lesion composition from a skin or a disinfectant, or wherein the container comprises at least two additional compartments, wherein one compartment comprises the solution for removing the cutaneous lesion composition and the second compartment comprises a disinfectant.

18. Kit, comprising a composition according to claim 1, and optionally in addition comprising a disinfectant and/or a solution for removing a dressing on the cutaneous lesion and/or a means for applying the composition.

19. The composition according to claim 1, wherein the composition comprises peroxides selected from the group consisting of $Na_2CClO_6$, $Na_2Cl_2O_6$ and peroxychlorate adducts from $Na_2CClO_6$, $Na_2Cl_2O_6$, and the composition contains less than 0.001 weight percent of other peroxides.

* * * * *